United States Patent [19]

Saurenman

[11] 4,078,943

[45] Mar. 14, 1978

[54] METHOD FOR CLEANING AND DISINFECTING MEDICAL EQUIPMENT

[75] Inventor: Dean F. Saurenman, Pearland, Tex.

[73] Assignee: Del Tek, Inc., Pearland, Tex.

[21] Appl. No.: 803,499

[22] Filed: Jun. 6, 1977

Related U.S. Application Data

[60] Continuation of Ser. No. 648,471, Jan. 12, 1976, abandoned, which is a division of Ser. No. 462,299, Apr. 19, 1974, Pat. No. 3,991,779.

[51] Int. Cl.$^2$ .......................... B08B 3/06; B08B 3/10; B08B 9/00
[52] U.S. Cl. ............................................ 134/14; 21/2; 134/22 C; 134/23; 134/25 R; 134/33; 134/34
[58] Field of Search ................ 134/56 R, 56 D, 57 R, 134/57 D, 95, 102, 157, 159, 25 R, 25 A, 22 C, 23, 14, 33; 21/98, 99, 105, 107, 2, 96, 58, 59, 97

[56] References Cited

U.S. PATENT DOCUMENTS

| 2,202,344 | 5/1940 | Hamilton et al. | 134/33 |
| 2,677,630 | 5/1954 | Scales | 134/23 |
| 3,739,791 | 6/1973 | Fry et al. | 134/157 |
| 3,853,622 | 12/1974 | Rutten | 134/25 R |

*Primary Examiner*—R.E. Serwin
*Assistant Examiner*—Bradley Garris

[57] ABSTRACT

A system for cleaning and disinfecting medical parts which include a drum rotatable about a horizontal axis where the drum includes an interior enclosable chamber for receiving small parts and circumferential retaining members for receiving and retaining tubular members about the horizontal axis. A timing device sequentially controls the operation upon filling by washing, draining, rinsing and drying in sequence and structure is provided to accomplish these functions.

8 Claims, 5 Drawing Figures

METHOD FOR CLEANING AND DISINFECTING MEDICAL EQUIPMENT

This application is a continuation application of a divisional application, Ser. No. 648,471, filed Jan. 12, 1976, now abandoned, from the patent application Ser. No. 462,299, filed Apr. 19, 1974, now U.S. Pat. No. 3,991,779.

BACKGROUND OF THE INVENTION

This invention relates to apparatus for cleaning and disinfecting medical equipment, and more particularly, to machine operated functions to improve cleanliness and disinfection of medical equipment.

Hospital acquired infections pose serious problems, and, to a large extent, may be a function of the cleaning and disinfecting procedures. It is established procedure to use hand washing techniques for cleaning and disinfecting. In recent years, technology has brought an abundance of throwaway parts and tubing to the medical profession. Nonetheless, it is desirable and it may become more necessary in the future for ecological purposes to clean and disinfect medical equipment for reuse.

Cleaning and disinfecting techniques for medical equipment should include, in addition to a thorough cleaning, removal of all organic matter, destruction of vegetative organisms, removal of all traces of detergent or other chemical additives, and adequate drying. Hand washing techniques are imprecise and are not as effective as machine washing techniques. Machine washing techniques can provide clear advantages over hand washing, provided that the apparatus is capable of achieving the desired cleaning, disinfecting and drying. Accordingly, it is the purpose of the present invention to provide new and improved machine cleaning and disinfecting systems for medical equipment.

SUMMARY OF THE INVENTION

The present invention includes an apparatus which can machine wash and disinfect, rinse and spray medical equipment in an automatic time cycle. The apparatus has a side loaded, rotatable washing drum which has a separate compartment for receiving small parts for cleaning and disinfecting. A circumferentially disposed set of negator springs permit a looping of tubing about the rotational axis for the drum and retention of the tubing relative to the drum so that rotation induces and forces flow of liquid through the tubing. Means are provided to fill the drum with wash water and add a disinfectant. Rotation of the drum for a wash period is timed by a timing mechanism which causes draining of the drum following the wash, spray rinsing and finally the application of a forced draft of hot air during a drying period. The drying system includes a hot air duct system to draw air through a vertical, chemically treated filter to a fan and heater which forces air into the drum.

BRIEF DESCRIPTION OF THE DRAWINGS

The drawing illustrating features of the present invention in conjunction with the specification include.

DESCRIPTION OF THE INVENTION

Figure 1:
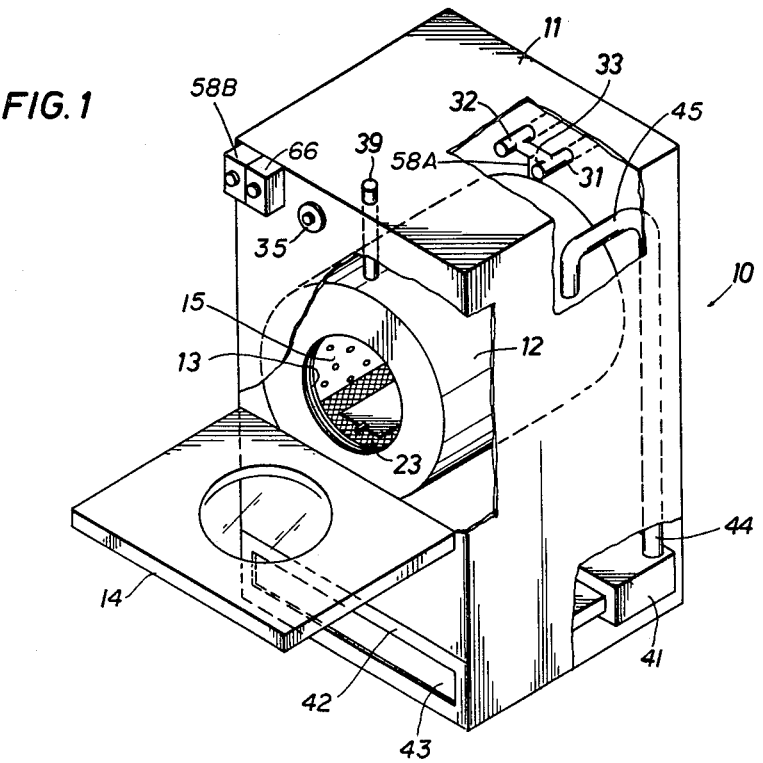
FIG. 1 which is a perspective representation of the organization and some details of the apparatus of the present invention.

Referring now to the drawings, an apparatus 10 for cleaning and disinfecting rubber, plastic, glass or metal medical parts or equipment is illustrated in FIG. 1. The apparatus of the present invention includes some common components and functional relationships to existing household washing machines which will be apparent from the discussions which follow. The apparatus 10, as shown in FIG. 1, has a typical rectangular outer configuration and a front opening. This style of apparatus is sometimes referred to as a "side-loading" machine because of the side opening. The apparatus 10 includes a frame and cabinet assembly 11 which houses a stationary tub 12 with a side opening 13. A hinged door 14 on the frame is arranged to seal with respect to the tub opening 13 so that the tub and door provide an enclosed liquid disinfectant washing chamber. The tub 12 is constructed of corrosion resistant material or is porcelain coated. The tub is a cylindrically shaped container. Concentrically arranged within the tub 12 is a perforated, porcelain coated, cylindrically shaped drum 15 with a cylindrically shaped, side opening 17 (FIG. 2) disposed and aligned with tub opening 13. The drum 15 is supported within the tub for rotation by means of a central axle 18 (FIG. 2) which is sealingly received by and rotatively supported by a tub bearing 19. The center axis for the tub bearing 19 is the axis of rotation for the drum 15. A pulley and belt connection 20 external to the tub 12 couples the axle 18 to an electrical driving motor 21. Thus, the motor 21 provides a driving means for rotating the drum 15 within the tub 12. The tub 12 is stationary and connected to the frame.

Figure 2:
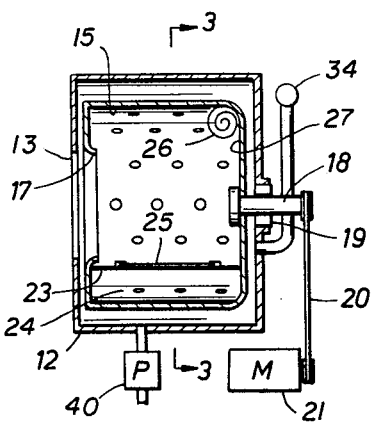
FIG. 2 which is a cross-section view and schematic representation of the washing apparatus.
Figure 3:
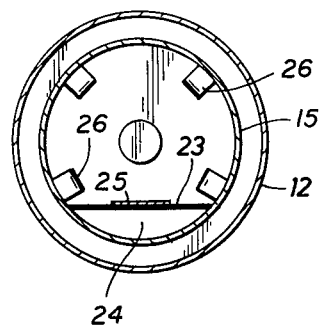
FIG. 3 which is a cross-section view taken along Line 3—3 of FIG. 2.

Within the drum 15, along a chord of its cylindrical shape is a transverse, flat, perforated surface 23, which together with the corresponding circular arc segment of the drum, forms an enclosure or chamber 24 within the drum. An access lid 25 is hinge connected across an opening in the surface 23 and a clasp is provided for retaining the lid in a closed position. In the remaining open area of the drum 15 are four circumferentially spaced negator type springs 26. A spring 26, as shown in FIGS. 2 and 3, has one outer end attached to a cylindrical wall of the drum and is curled so that the opening between adjacent coil surfaces faces toward the rearward side wall 27 of the drum. In the practice of the present invention, small parts to be cleaned are disposed in Chamber 24. Tubing to be cleaned is disposed within the drum in a circular fashion by being inserted into the center spacing between the negator spring coils 26 so that the springs retain the tubing in a cylindrical manner within the drum 15. The springs contract upon the tubing to hold it in position relative to the drum and can be expanded or contracted by their spring action to handle various sizes of tubing coils.

In the practice of the present invention, the parts and/or tubing to be chemically disinfected are placed within the enclosure 24 and the rotatable drum and secured in place. The door 14 is closed and the operation initiated by beginning the fill cycle. During the fill cycle, the drum is rotated by the motor 21 while hot wash water and a cleaning disinfectant are introduced into the tub. The wash water is introduced from input supplies (not shown) which are respectively connected to hot and cold water inlet valves 31 and 23 (see FIG. 1). The outlets for the valves 31 and 32 couple to a common input pipe 33 which enters to the tub so that a temperature mixed water is injected into the tub. A water level 34 is schematically illustrated in FIG. 2 as attached to the tub 12. The water level valve 34 is operated by the level of water relative to a predetermined point or level in the tub. This level is below the tub opening 13 so that water does not overflow from the tub. The water level valve 34 closes one set of electrical contacts when the water level is above the predetermined point and closes another set of electrical contacts, when or if the water level is below the predetermined point. The water level valve 34 is used to initiate operation of a cycle timing motor and to control operation of the water inlet valves. To actuate the water inlet valves 31 and 32, a conventional switch and timing control knob 35 is used. The timing control knob is a part of a cycle timing system to initiate a cycle of operation which includes filling the tub with water, rotating the drum, pumping out the water, spraying, and drying by hot air. As will be apparent from the discussion to follow, the cycle is automatic. The disinfectant is introduced into the tub 12 by means of a vertical tube 39 which extends between the outside of the cabinet and the interior of the tub 12. The tube 39 also serves as a choke outlet for the hot air drying.

After the water level in the tub reaches the predetermined point and the disinfectant is added, the drum 15 continues rotation for a time period adequate to wash and disinfect the components within the tub. After the washing period, the timing motor (which was actuated by the water level valve 34) discontinues or disconnects the water valves 31 and 32 from operation and a discharge pump 40 (FIG. 2) is actuated to discharge the liquid from the tub. Following this, the water valves 31 and 32 can be actuated for rinsing or spray purposes. After rinsing, the pump operation is discontinued and a drying cycle is initiated. For the hot air drying cycle, as shown in FIG. 1, a heating and fan unit 41 is connected to a front opening inlet 42. A disinfecting bacteriostatic filter means 43 are disposed in the opening inlet 42 to treat the input air to the fan unit 41. The output of fan unit 41 is to a vertical pipe 44 which has a "U" shaped return bend 45 located above the tub 12 and which opens to the upper surface of the tub. This "U" shaped configuration located above the tub prevents liquid from access to the drying system.

Figure 4:
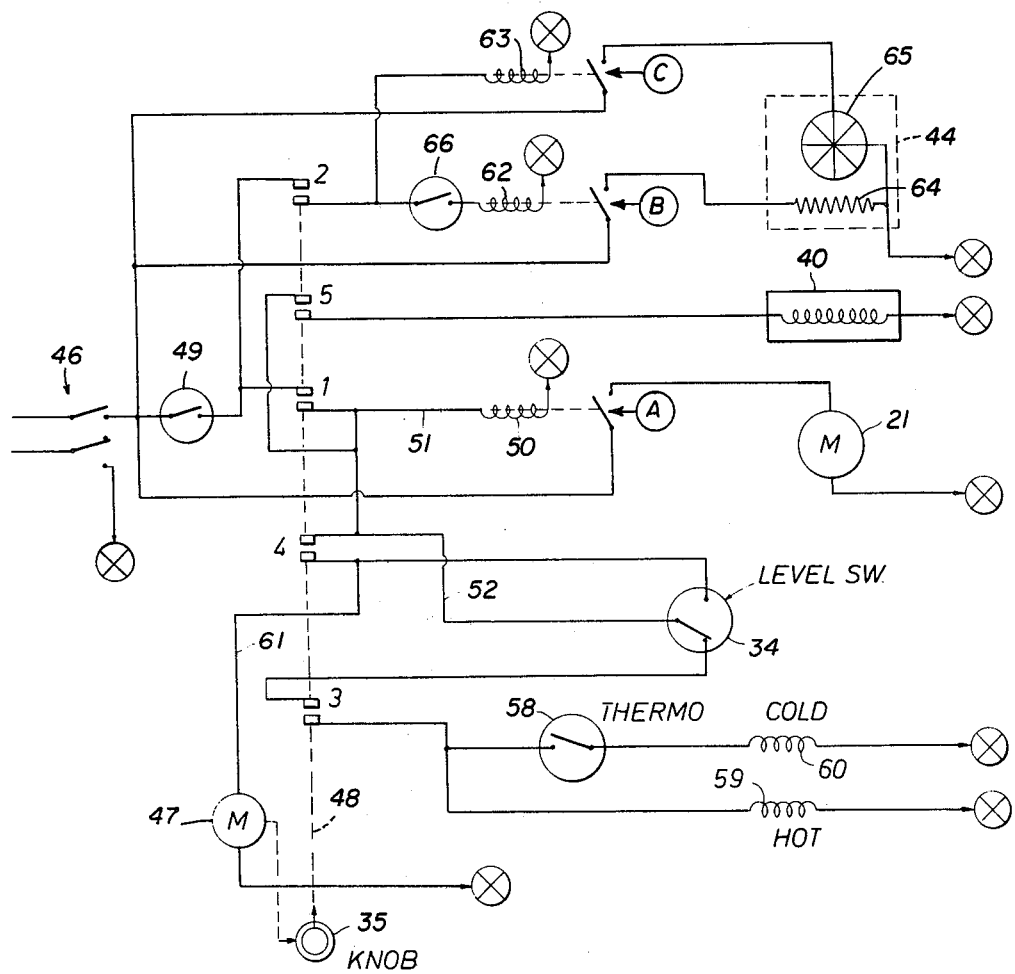
FIG. 4 which is a schematic illustration of the electrical circuitry.
Figure 5:
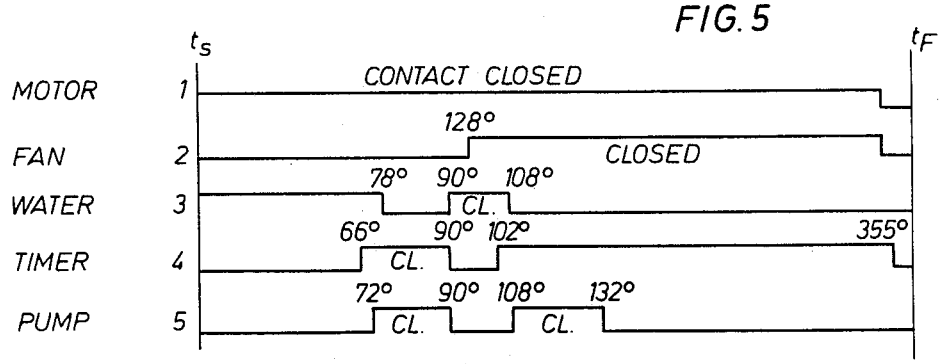
FIG. 5 which is a timing diagram for the sequence of operation.

Referring now to FIG. 4, an electrical schematic layout illustrates the various electrical components while FIG. 5 illustrates a timing sequence. At a time $T_S$, a main manual switch 46 is thrown to apply an alternating current from a power supply to the electrical system of the unit. The manual switch 46 may be incorporated in the push-pull rotating knob switch 35, if desired. The rotating knob switch 35 includes a timer motor 47 to produce a 360° rotation of the knob switch 35 and an associated cam shaft illustrated by the dashed line 48. The cam shaft 48 has cams (not shown) thereon which control the opening and closing of switches 1–5 throughout the time that the shaft 48 is rotated by the timer motor 47. At the time $T_S$, the cams for switch 1 and 3 cause the switch contacts to assume a closed condition. Switch 1 has its contacts closed for 351° of the cam shaft rotation from the time $T_S$. The manual switch 46 is in series with a door switch 49 and one of the switch 1 contacts so that upon the closing of the door 14 on the machine and switch 46, electrical power is applied to switch 1 contacts and thence to a solenoid switch relay coil 50 to a conductor 51 and to the water level switch 34 by a conductor 52. The solenoid relay 50, when energized, closes a heavy duty switch "A" which applies operating power from the electrical source to the motor 21 so that the drum 15 is rotated. The water level switch 34, in the position shown for its contacts, connects the switch 1 contacts to the switch 3 contact. The switch 3 contacts are closed for the initial 78° of the cam shaft rotation, opened between cam shaft positions of 78° and 90°, closed between cam shaft positions of 90° and 108°, and then opened for the remainder of the cam shaft rotation through 360°. When the switch 3 contacts are closed, electrical power is applied to a thermostat control switch 58 and to a hot water solenoid coil 59. The solenoid coil 59, when energized, operates the hot water valve 32 to admit water to the inlet pipe 33. As illustrated in FIG. 1, the the thermostat sensor 58A is in the water inlet line 33 and when the temperature level reaches the thermostat setting, the thermostat switch 58 closes its contacts so that a cold water solenoid 60 is energized to operate the cold water valve 31 to supply cold water to the inlet pipe 33. When the temperature decreases to the lower thermostat level, the contacts of the thermostat switch are opened, and the cold water solenoid coil 60 is de-energized. The control switch 58 is adjustable by a control 58B to any desired temperature.

Next in the sequence of operation, the water level in the drum reaches a predetermined level and the water level switch 34 is operated to disconnect the switch 1 contacts and the power supply from the water valve control solenoids 59 and 60. The water level switch 34 when it changes contact positions, connects the switch 1 contacts to the switch 4 and to the timer motor 47 via a conductor 61. The time motor 47, in turn, produces a rotation of the timer knob 35 and cam shaft 48 to provide the automatic control of the operation.

Just prior to the time that switch 3 contacts are opened at 78° of the cam shaft rotation, the switch 4 contacts are closed at 66° of cam shaft rotation. The closing of switch 4 contacts maintains power to the time motor 47 even if the water level switch 34 changes position. Switch 4 contacts are closed between 66° and 90° of cam shaft rotation and from 102° of cam shaft rotation to the end of the cycle.

The switch 5 contacts are closed by the cam shaft rotation between 72° and 90° and between 108° and 132°. Closing of the switch 5 contacts energizes the coil of the pump 40 to discharge water during these time periods.

The switch 2 contacts are closed from 128° through 351° of the cam shaft rotation. Closing of switch 2 contacts energizes solenoid coils 62 and 63 for the power relay switches B and C. Power relay switch B couples the electrical power to a Cal-Rod heating element 64 in the fan unit 41 while power relay switch C couples the electrical power to the fan element 65. An adjustable thermostat switch 66 is located in the connection to the coil 62 so that the temperature of the hot air can be controlled. The sensing element for the thermostat can be located in the outlet vent pipe 39.

The following table may be helpful in relation to the timing cycle.

TABLE 1

| MINUTES | FUNCTION |
| --- | --- |
| 0 to fill | Tub filled with regulated temperature water and disinfectant added |
| Full - 11 | Wash |
| 11 - 15 | Drain, and spray rinse |
| 15 - 18 | Water rinse |
| 19 - 22 | Drain |
| 19 - 59 | Hot air dry |

In the operation of this invention, an air drying temperature of about 145° F is satisfactory. A water temperature of 145° F to 170° F for washing has been found as satisfactory.

The fan and heating unit can be a squirrel cage blower and a "Cal-Rod" heating element where the hot air outlet duct to the tub is 3 inches in diameter and the vent pipe from the tub is 1 inch in diameter. The 1 inch outlet diameter from the tub restricts the outlet air flow and retains the heat in the tub for effective drying. The speed of the drum is constant between 40 to 45 RPM.

The negator springs 26 can be berrylium copper. Their gripping power is a function of width and thickness and can be adjusted as desired. The filter 43 is a polyester material 4 inches thick which is treated with "Consan 20" to make it bacteriostatic. This can be four layers of 1 inch thick material. The chemical treatment involves dipping the filter in a solution of 2½ oz. of Consan 20 per gallon of water and drying the filters. It will also be noted in connection with the filter and air opening that they are in a vertical plane. This takes advantage of the fact that bacteria does not adhere to vertical walls. The amount of wash water used is about 7 gallons and, of course, is a function of tub size.

In summary, the enclosure is filled with medical equipment parts small enough to be put in the compartment 24. The compartment enclosure 24 should preferably be over-filled so that when the lid is closed, the equipment is pressed in and hence tumbling of parts is prevented. Rubber parts such as masks should be included in the enclosure whenever possible to help hold the parts immobile and to act as a cushion. Tubings are coiled in the drum and fastened by the negator springs 27 so that a tubing coil revolves just as the drum does. The tubings are tucked between the negator spring coils and the outer diameter of the drum.

When the door 14 of the machine is closed, the power can be turned on. The disinfectant, such as ½ oz. of "Consan 20" should be added through the fill vent 39. When the tub 12 is filled with water to the washing level, the automatic cycle is started by the level valve 34 and the parts are cleaned and disinfected during the cycle of operation.

While particular embodiments of the present invention have been shown and described, it is apparent that changes and modifications may be made without departing from this invention in its broader aspects; and therefore, the aim in the appended claims is to cover all such changes and modifications as fall within the true spirit and scope of this invention.

What is claimed is:

1. A method for cleaning and disinfecting tubing used in medical applications comprising the sequential steps of
    disposing said tubing in a circular fashion about a non-vertical axis in a cylindrical drum rotatably disposed with respect to said non-vertical axis,
    filling such drum partially with a disinfecting and cleaning liquid, and
    rotating said drum and attached tubing so as to force liquid through said tubing in response to rotation of said tubing about said non-vertical axis and through said disinfecting and cleaning liquid.

2. The method as defined in claim 1 wherein said non-vertical axis is generally horizontal and said disposing step includes releasably attaching said tubing to a wall of said cylindrical drum.

3. The method as defined in claim 2 and including the further step of rinsing said tubing with a rinse liquid after rotating said tubing through said disinfecting and cleaning liquid.

4. The method as defined in claim 3 and including the further step of drying said tubing with bacteriostatically filtered hot air.

5. A method for cleaning and disinfecting tubing used in medical applications comprising the sequential steps of disposing said tubing in a circular manner about an axis, releasably attaching said tubing to a wall member rotatable about such axis where said wall member is disposed so as to rotate with respect to an enclosure, partially filling said enclosure with a disinfecting and cleaning liquid, rotating said wall member and tubing about said axis so that said wall member and tubing are repeatedly immersed in said liquid and rotation of said wall member forces said liquid through said tubing.

6. A method for cleaning and disinfecting tubing used in medical applications comprising the sequential steps of
    coiling a length of tubing about an axis in a hollow retaining member so that the turns of the tubing are disposed about such axis and releasably positioning said tubing relative to the retaining member,
    partially filling a drum enclosing said retaining member with a disinfecting and cleaning liquid; and
    rotating said retaining drum and releasably positioned tubing so as to force such disinfecting and cleaning liquid through said tubing in response to rotation of said tubing about such axis and through said disinfecting and cleaning liquid.

7. A method for cleaning and disinfecting tubing used in medical applications comprising the sequential steps of positionally coiling tubing about a rotational axis in a hollow retaining member where said hollow retaining member is rotatable about such rotational axis, partially filling an enclosure containing said retaining member with a disinfecting and cleaning liquid, rotating said retaining member and tubing about said rotational axis so that the tubing in said liquid is passed through said liquid and rotation of said retaining member forces said liquid through said tubing.

8. The method as defined in claim 7 wherein said coiling step includes releasably fixing such tubing with respect to the hollow retaining member.

* * * * *